United States Patent [19]

Takahashi et al.

[11] Patent Number: 4,812,406
[45] Date of Patent: Mar. 14, 1989

[54] PROCESS FOR PREPARING OPTICALLY ACTIVE HYDANTOINS

[75] Inventors: Satomi Takahashi, Kobe; Yukio Yamada, Kakogawa; Yasuyoshi Ueda; Yasuhiro Katayama, both of Takasago; Yoshio Shimada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 775,090

[22] Filed: Sep. 12, 1985

[30] Foreign Application Priority Data

Sep. 17, 1984 [JP] Japan .................. 59-195392

[51] Int. Cl.$^4$ .................. C12P 17/10; C12P 13/04
[52] U.S. Cl. .................. 435/280; 435/121; 435/106
[58] Field of Search .................. 435/280, 253, 121, 106

[56] References Cited

U.S. PATENT DOCUMENTS

| | | | |
|---|---|---|---|
| 3,964,970 | 6/1976 | Dinelli et al. | 435/115 |
| 4,237,227 | 12/1980 | Yamada et al. | 435/280 |
| 4,312,948 | 1/1982 | Olivieri et al. | 435/253 |
| 4,418,146 | 11/1983 | Lungershausen et al. | 435/227 |

FOREIGN PATENT DOCUMENTS

| | | |
|---|---|---|
| 0037672 | 10/1981 | European Pat. Off. |
| 0152977 | 8/1985 | European Pat. Off. |
| 2310986 | 12/1976 | France |

OTHER PUBLICATIONS

Lehninger, 1975, Biochemistry, 2nd Ed., Worth Publishers, Inc., pp. 189–191 and 202–205.

Primary Examiner—Esther M. Kepplinger
Attorney, Agent, or Firm—Armstrong, Nikaido, Marmelstein & Kubovcik

[57] ABSTRACT

A process for preparing optically active hydantoins having the general formula (II):

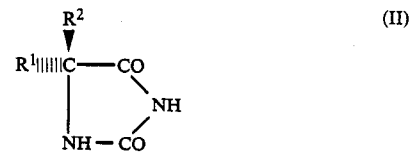

wherein $R^1$ and $R^2$, which are different from each other, are independently alkyl group, aralkyl group, aryl group, substituted alkyl group, substituted aralkyl group, or substituted aryl group, or $R^1$ and $R^2$ form an asymmetric cyclic compound, characterized in that one configuration of racemic N-carbamoyl-α-amino acid having the general formula (I):

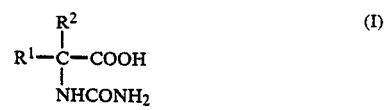

wherein $R^1$ and $R^2$ are as above, is enzymatically converted into the corresponding hydantoins.

The present invention provides a process for an optical resolution with a high efficiency which can be used for the synthesis of (S)-6-fluoro-spiro-[chroman-4,4'-imidazolidine]-2',5'-dione (USAN; Sorbinil), which is an optically active hydantoins attracting public attention as a preventive or a remedy for the particular chronic symptoms of diabetes such as cataract and neuropathy, and (S)-α-methyl-3,4-dihydroxyphenylalanine (L-methyldopa), which is an optically active amino acid widely used as antihypertensives. Further, the present invention provides a novel finding that N-carbamoyl-α-amino acid having no hydrogen atom on its α-carbon atom can be biochemically converted into hydantoins by an enzymatic cyclization reaction.

16 Claims, No Drawings

PROCESS FOR PREPARING OPTICALLY ACTIVE HYDANTOINS

BACKGROUND OF THE INVENTION

The present invention relates to a process for an optical resolution of racemic N-carbamoyl-α-amino acid by converting N-carbamoyl-α-amino acid into optically active hydantoins by a stereo-selective enzymatic reaction. According to the present invention, an optically active compound useful as a drug or a synthetic intermediate thereof can be produced with great advantage.

One of the object of the invention is to effectively produce optically active hydantoins. hydantoins of many varieties are known and many of them are used as a drug such as anticonvulsants or antipsychotic agents.

Generally, racemic hydantoins are employed. However, for improving the efficiency and reducing a side effect, using hydantoins in an optically active form is more preferable since, in many cases, only those having a particular configuration can show a physiological activity when the hydantoins have an asymmetric carbon atom.

Hitherto, the following processes have been known for preparing optically active hydantoins, i.e. (1) a process which comprises that optically active α-amino acid is reacted with an alkali metal salt of cyanic acid to give N-carbamoyl-α-amino acid, which is then heated in a mineral acid to cyclize into hydantoins, (2) a process which comprises that cyanoacetic acid is converted into isocyanate, which is reacted with amines to give N-carbamoylaminonitryl, which is finally heated in a mineral acid to cyclize into hydantoins, (3) a process which comprises that optically active brucine is added to racemic hydantoins to form a salt of diastereoisomer, which is subjected to an optical resolution using a difference of solubility in the solvent (J. Med. Chem. 21(12), 1294, 1978), and (4) a process which comprises that ketone is reacted with optically active amine to give ketimine, to which hydrogen cyanide is added asymmetrically, and the resultant is reacted with chlorosulphonylisocyanate to give optically active hydantoins (J. Org. Chem. 47, 4081, 1982).

When an optically active amino acid can be obtained in a relatively easy way as in a case of natural amino acid, the process (1) is advantageous. However, when it is difficult to obtain an optically active amino acid, the process (1) and (2) usually require complicated procedures such as converting racemic compounds into acidic or basic derivatives, which is then subjected to an optical resolution, in order to obtain a starting material in an optically active form. The process (3), where racemic hydantoins are directly subjected to an optical resolution, needs brucine as a resolving agent, which has a strong toxicity, and thus this process meets many problems in the view point of workability and safety such as handling of brucine and a contamination of a product with brucine when an industrial scale production is expected. The process (4), where a desired compound in an optically active form is directly synthesized by an asymmetric synthesis, has many difficulties for practical use such as a consumption of more than an equimolar amount of expensive optically active amine and chlorosulphonyl isocyanate and a great difficulty of removal of undesired optically active portion which is derived from amine.

As the result of the inventors' extensive study on the hydantoins and N-carbamoyl-α-amino acid, which is easily obtained from the hydantions, to develop a process for efficiently synthesizing optically active hydantoins based on a biochemical technique, it has now been found that some microorganisms could produce optically active hydantoins by a stereo-selective cyclization reaction of the substrate N-carbamoyl-α-amino acid and said enzymatic reaction could be an effective means for an optical resolution, being of very wide application and effective for the production of optically active amino acid as well as an optically active hydantoins.

SUMMARY OF THE INVENTION

An outline of the present invention is shown in the following scheme:

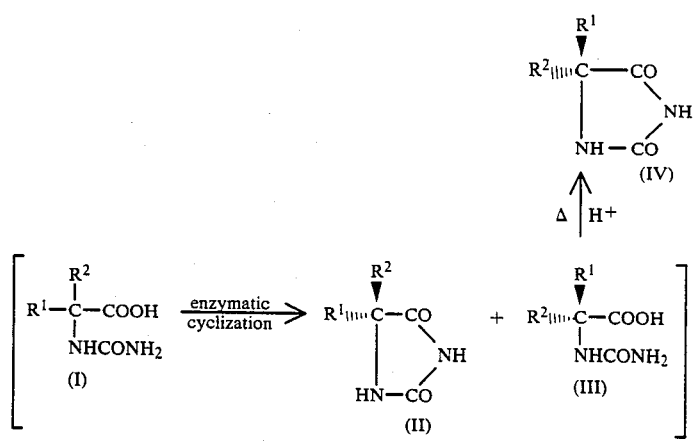

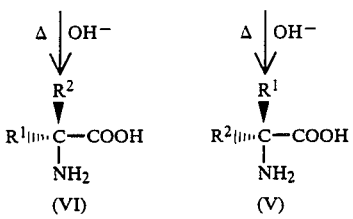

wherein $R^1$ and $R^2$, which are different from each other, are independently alkyl or alkenyl group, preferably $C_1$ to $C_{12}$; aralkyl group, preferably $C_6$ to $C_{12}$; aryl group, preferably $C_4$ to $C_{12}$; alkyl or alkenyl group substituted with a halogen, hydroxyl, alkoxy, nitro, cyano, carboalkoxy group or heterocyclic ring such as

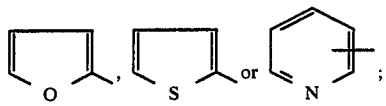

aralkyl or aryl group substituted with not less than one of a halogen, hydroxyl, alkoxy, nitro, cyano, carboalkoxy or methylenedioxy group; or $R^1$ and $R^2$ form an asymmetric ring such as the group of the formula:

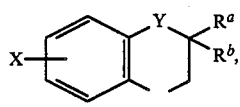

wherein X is a halogen, Y is selected from the group consisting of O, NH, S, SO, $SO_2$ and $(CH_2)_n$, wherein n is 0 or integer 1, $R^a$ and $R^b$ are hydrogen atom or methyl group, or the group of the formula:

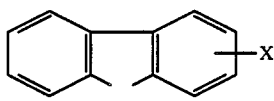

wherein X is as above.

The present invention provides a process for preparing optically active hydantoins which comprises enzymatically converting one configuration of racemic N-carbamoyl-α-amino acid having the general formula (I) into hydantoins having the general formula (II) and separating the unreacted enantiomer of N-carbamoyl-α-amino acid as an optically active N-carbamoyl-α-amino acid having the general formula (III) which has an opposite configuration to, the obtained hydantoins. Moreover, the thus obtained enantiomer of N-carbamoyl-α-amino acid having the general formula (III) can be easily converted into optically active hydantoins having the general formula (IV) without changing the configuration by heating N-carbamoyl-α-amino acid having the general formula (III) in an acidic condition to cyclize, and thus, the present invention can be also referred to as a process for an optical resolution of racemic N-carbamoyl-α-amino acid into the optically active hydantoins having the general formula (II) and (III). Further, both optically active hydantoins having the general formula (II) and the enantiomer of N-carbamoyl-α-amino acid having the general formula (III) can be converted by hydrolysis with alkali into the corresponding optically active N-carbamoyl-α-amino acids having the general formula (IV) and (V) respectively, and thus, the present invention can be also referred to as a process for an optical resolution of racemic N-carbamoyl-α-amino acid into the corresponding optically active amino acid.

DETAILED DESCRIPTION

The racemic N-carbamoyl-α-amino acid used in the present invention as a starting material can be easily synthesized by synthesizing N-carbamoyl-α-amino acid starting from ketone by Strecher method or Bucherer method both of which are well-known methods for a synthesis of α-amino acid and reacting the obtained α-amino acid with an alkali metal salt of cyanic acid. Alternatively, the N-carbamoyl-α-amino acid can be directly synthesized by hydrolyzing hydantoins which are synthetic intermediates in the Bucherer method under controlled conditions.

Enzymes used in the present invention can be usually obtained by cultivating microorganisms. The microorganisms which can produce optically active hydantoins by a stereo-selective cyclization of the N-carbamoyl-α-amino acid are in the wide range of species. Examples of such microorganisms belonging to the bacteria are, for instance, Aerobacter, Agrobacterium, Bacillus, Corynebacterium, and the like and example of such microorganism belonging to actinomyces is, for instance, Nocardia.

Cultivation of these microorganisms is usually carried out in a liquid nutrient medium. The culture medium contains assimilatable source of carbon, source of nitrogen, and an inorganic salt which is an essential nutrient for a growth of the microorganisms. A small amount of enzyme-inducer such as a base constituting nucleic acid and derivatives thereof is preferably added to the culture medium and thereby a relevant enzyme is adaptively reinforced. A temperature at cultivation ranges from 20° to 70° C. and pH from 4 to 10. It is also possible to accelerate the growth of the microorganisms by an aerated stirring.

In the cyclization reaction of N-carbamoyl-α-amino acid into hydantoins, a cultured broth, cells, or treated cells obtained as mentioned above can be used as enzymes. Though a cultured broth of the microorganisms can be used as it is, cells separated from a cultured broth are more preferably used. Dried cells such as lyophilized cells can be also used as well as living cells. Further, grinded cells or extracts of the cells can be used as enzymes in the reaction.

A concentration of the substrate N-carbamoyl-α-amino acid in the reaction solution may range from 0.1 to 30%. Preferably, a pH value of 5 to 8 is employed in the reaction. When a pH value is below 5, the enzymes are apt to be made inactivated. When a pH value is over 8, it becomes difficult to complete the reaction due to an increase of solubility of hydantoins, not being suited for a practical use. Though an optimum pH value varies depending on the reaction substrate and the employed enzymes, it ranges from about 5 to about 8. Preferably, an optimum pH value is maintained by adding heutralizing agent from time to time since a pH value shifts toward alkaline side as a progress of the cyclization reaction. Suitable neutralizing agent is a mineral acid such as hydrochloric acid or sulfuric acid. The reaction is carried out at the reaction temeprature ranging from 30° to 60° C. and at a temperature suited for the employed enzymes. By adjusting the above reaction conditions and an amount of the enzymes, nearly quantitative conversion can be achieved in a relatively easy way and also the unreacted N-carbamoyl-α-amino acid as an optically active enantiomer can be isolated in a very high purity.

After the enzymatic cyclization reaction, the produced optically active hydantoins and the unreacted enantiomer of N-carbamoyl-α-amino acid can be isolated by the know method. Generaly, hydantoins which have no hydrogen atom in its α-carbon atom such as those formed in the process of the present invention are slightly soluble in an aqueous medium at a pH value of 8 to 9. Therefore, hydantoins are formed in the present cyclization reaction mostly in the form of a precipitated crystal. When a pH value is over 11, however, the hydantoins become salts of alkali metal and show a high solubility. On the other hand, the substrate N-carbamoyl-α-amino acid becomes a salt of alkali metal under the reaction condition of the present invention (pH 5 to 8), which shows an extremely high solubility and allows a complete resolution. When a pH value is not more than 4, however, the N-carbamoyl-α-amino acid becomes extremely insolubile due to free carboxylic group thereof. By utilizing a change of a solubility of the hydantoins and the N-carbamoyl-α-amino acid in an aqueous medium based on a pH value, it is possible to separate and isolate the formed hydantoins and the unreacted N-carbamoyl-α-amino acid in a quite easy way. Also, they can be easily separated and isolated by an extraction method according to a high solubility in an organic solvent such as ethyl acetate.

The unreacted enantiomer of N-carbamoyl-α-amino acid can be easily cyclized into optically active hydantoins by a known method of heating to 70 to 100° C. under stirring in a mineral acid such as hydrochloric acid or sulfuric acid or an organic acid such as acetic acid. It is also possible to convert the N-carbamoyl-α-amino acid into an optically active amino acid by hydrolyzing the N-carbamoyl-α-amino acid with an alkali metal hydroxide such as sodium hydroxide, potassium hydroxide and barium hydroxide or by oxidizing carbamoyl group with an equimolar amount of sodium nitrite in a mineral acid.

It is needless to say that an efficiency of the present invention is further improved by converting the undesirable enantiomer which is unavoidably produced in the present invention into the corresponding N-carbamoyl-α-amino acid by such a process as hydrolysis with alkali and oxidizing the obtained α-amino acid into ketone by a known method using an oxdizing agent such as hypohalogenous acid, said ketone being converted again into racemic N-carbamoyl-α-amino acid for a cyclic reuse.

The present invention provides a process for an optical resolution with a high efficiency which can be used for the synthesis of (S)-6-fluoro-spiro-[chroman-4,4'-imidazolidine]-2',5'-dione (USAN; Sorbinil), which is an optically active hydantoins attracting public attention as a preventive or a remedy for the particular chronic symptoms of diabetes such as cataract and neuropathy, and (S)-α-methyl-3,4-dihydroxyphenylalanine (L-methyldopa), which is an optically active amino acid widely used as antihypertensives. Further, the present invention provides a novel finding that N-carbamoyl-αamino acid having no hydrogen atom on its α-carbon atom can be biochemically converted into hydantoins by an enzymatic cyclization reaction.

The present invention is more particularly described and explained by the following Examples. It is to be understood, however, that the present invention is not limited to the Examples and various changes and modifications can be made without departing from the spirit and scope of the present invention.

EXAMPLE 1

After preparing a liquid nutrient medium having the following composition, each 500 ml shaking flask stuffed with cotton was filled with 100 ml of the medium and steam-sterilized at 120° C. for 20 minutes.

| [composition] | |
| --- | --- |
| meat extract | 0.5% by weight |
| yeast extract | 0.5% |
| polypentone | 1.0% |
| NaCl | 0.15% |
| uracil | 0.10% |
| $MnCl_2 \cdot 4H_2O$ (pH 7.0) | 20 ppm |

A loop of microorganisms shown in Table 1, each cultures of which are freely available to the public generally without restriction, and previously cultivated on bouillon agar slant at 30° C. for 24 hours was inoculated into the above nutrient broth and subjected to a shake culture at 33° C. for 24 hours. After centrifugation of 40 ml of the culture solution, the obtained living cells were washed with 40 ml of 0.9% aqueous solution of salt. After further centrifugation, cells suspension was prepared by adding 0.9% aqueous solution of salt to the cells so as to become 10 ml as a total amount.

For the reaction, the following solution and suspension were prepared.

(1) A solution of 250 μ mole of the substrate (RS)-N-carbamoyl-α-phenylglycine or (RS)-4-carbamoylamino-6-fluorochroman-4-carboxylic acid dissolved in 0.1M phosphate buffer solution (pH 7.2) and prepared to become 2.5 ml as a total amount (2) The cells suspension prepared as mentioned above: 2.5 ml The above solution (1) and the suspension (2) were put into a small test tube with stopper and the mixture was reacted at 37° C. for 48 hours, stirring with a magnetic stirrer. A solution of substrate (1) not added with the cells suspension was also subjected to the same reaction condition as a control. After the reaction was completed, a portion of the reaction mixture was sampled and an amount of 4-methyl-4-phenyl-imidazolidine-2,5'-dione or 6-fluoro-spiro-[chroman-4,4'-imidazolidine]-2',5'-dione formed in the reaction system was determined by high performance liquid chromatography.

Column: Finepak SIL $C_{18}$ (4.6 mm ID×250 mm) (made by Nippon Bunko Kogyo Kabushiki Kaisha)

Mobile phase: 60 mM phosphate buffer solution (pH 2.5)/MeOH=83/17 (V/V)

Flow rate: 2.0 ml/min.
Detector: 210 nm
Internal standard: 4-(2-methylthioethyl)-imidazolidine-2,5-dione The results obtained in case of various microorganisms are shown in Table 1.

TABLE 1

| Microorganism | Amount of produced 4-methyl-4-phenyl-imidazolidine-2,5'-dione (μ moles) | Amount of produced 6-fluoro-spiro-[chroman-4,4'-imidazolidine-2',5'-dione (μ moles) |
| --- | --- | --- |
| Aerobacter cloacae IAM 1221 | 80 | 26 |
| Agrobacterium rhizogenes IFO 13259 | 30 | 18 |
| Bacillus badius IAM 11059 | 58 | 33 |
| Bacillus species KNK 108 | 125 | 125 |
| Bacillus stearothermophilus* IFO 12550 | 38 | 15 |
| Corynebacterium sepedonicum IFO 3306 | 104 | 76 |
| Corynebacterium sepedonicum IFO 13259 | 77 | 51 |
| Nocardia corallina IFO 3338 | 110 | 25 |

*Both cultivation and reaction was carried out at 50° C.

Any of the formed imidazolidine derivatives were optically active (R)-form with respect to 4-carbon atom of imidazolidine.

EXAMPLE 2

After preparing a liquid nutrient medium having the following composition, each of 500 ml shaking flask stuffed with cotton was filled with 150 ml of the medium and steam-sterilized at 120° C. for 20 minutes.

| [composition] | |
| --- | --- |
| meat extract | 2.0% (W/V %) |
| glucose | 0.8% |
| NaCl | 0.3% |
| uracil | 0.1% |
| pH | 7.5 |

A loop of Bacillus species KNK 108 (FERM P-6056) which was previously cultivated on bouillon agar slant at 30° C. for 20 hours was inoculated into the above medium and subjected to a shake culture at 33° C. for 22 hours.

After centrifuging 200 ml of the culture solution, the obtained cells were washed with 200 ml of 0.9% aqueous solution of salt. After further centrifugation, the cells suspension was prepared by adding 0.9% aqueous solution of salt to the cells so as to become 20 ml as a total amount.

For the reaction, the following solution and suspension were prepared.

(1) A solution of 1.20 g of (RS)-4-carbamoylamino-6-fluorochroman-4-carboxylic acid dissolved as a sodium salt (pH 7.2) and prepared to become 20 ml as a total amount (2) The cells suspension prepared as mentioned above A mixture of the above solution (1) and the suspension (2) was put into a 100 ml four-necked round flask and was reacted with stirring at 37° C. for 48 hours. During the reaction, a pH value in the reaction system was continuously maintained at 7.2 with a 0.5N HCl solution. After the reation was completed, the reation mixture was cooled and adjusted to a pH value of 7.0 and an insoluble mixture of the cells and a crystal precipitated in the reaction and a supernatent were separated by centrifugation. The thus obtained insoluble mixture was suspended in 50 ml of water followed by an extraction with 100 ml of ethyl acetate for two times. After distilling away ethyl acetate from the obtained extract under reduced pressure, a residue was recrystallized from ethanol to give 0.51 g of a white crystal.

The compound was identified as (R)-6-fluorospiro-[chroman-4,4-imidazolidine]-2',5'-dione by the following analytical values.

Nuclear magnetic resonance spectrum δ ppm (DMF-$d_7$): 2.1 to 2.6 (2H, m, $CH_2$), 4.1 to 4.8 (2H, m, $CH_2$), 6.8 to 7.2 (3H, m, aromatic), 8.4 (1H, s, NH), and 1.0 (1H, br s, NH).

Infrared absorption spectrum ($cm^{-1}$, KBr-disk): 3340, 3205, 1760, 1710, 1490, 1400, 1260 and 1160.

$[\alpha]_D^{25} = -55.0$ (c=1.0, MeOH).

Melting point: 241° to 242° C.

On the other hand, a white precipitate was formed by adjusting a pH value of the supernatent to 1.0 using a 6N HCl solution. The precipitate was filtered and recrystallized from ethanol to give 0.54 of a white crystal.

The compound was identified as (S)-4-carbamoylamino-6-fluorochroman-4-carboxylic acid by the following analytical values.

Nuclear magnetic resonance spectrum δ ppm (DMSO-$d_6$): 2.3 to 2.7 (2H, m, $CH_2$), 3.9 to 4.5 (2H, m, $CH_2$), 5.7 (2H, s, $NH_2$), 6.7 (1H, s, NH) and 6.8 to 7.4 (3H, m, aromatic).

Infrared absorption spectrum ($cm^{-1}$, KBr-disk): 3470, 3380, 1720, 1640, 1560, 1500, 1485, 1425, 1370 and 1260.

$[\alpha]_D^{25} = +112.7$ (c=0.5, MeOH).

Melting point: 196° to 197° C.
Melting point: 196° to 197° C.

EXAMPLE 3

To 10 ml of 2N HCl solution was suspended 400 mg of (S)-carbamoylamino-6-fluorochroman-4-carboxylic acid obtained in Example 2 and the mixture was reacted at 80° C. for 3.5 hours under stirring with a magnetic stirrer. After the reaction was completed, the resultant was allowed to stand in the refrigerator for a night. A precipitated crystal was filtered and dried under reduced pressure at 60° C. to give 340 mg of a white crystal.

Analytical values of the compound completely agreed with those of a sample of (S)-6-fluoro-spiro[chroman-4,4'-imidazolidine]-2',5'-dione.

$[\alpha]_D^{25} = -55.7$ (c=1.0, MeOH).

Melting point: 241.5° to 242.5° C.

EXAMPLE 4

To 500 ml of a cuture solution of Bacillus species KNK 108 (FERM P-6056) obtained by the same procedures as in Example 2 was added 15.0 g of (RS)-N-carbamoyl-α-methyl-3,4-methylenedioxyphenylalanine. After a mixture was adjusted to a pH value of 7.2 with 10N NaOH solution, it was reacted at 37° C. for 48 hours. During the reaction, a pH value in the reaction system was continuously maintained at 7.2 with 0.5N HCl solution. After the reation was completed, the reation mixture was cooled and adjusted at a pH value of 7.0 and an insoluble mixture of the cells and a crystal precipitated in the reaction and a supernatent were separated by centrifugation. A pH value of the thus obtained supernatent was adjusted to 1.0 by 6N HCl solution to form a white precipitate. After the precipitate was filtered and washed with water sufficiently, the resultant was dried under reduced pressure to give 7.3 g of a white crystal of (S)-N-carbamoyl-α-methyl-3,4-methylenedioxyphenylalanine.

Nuclear magnetic resonance spectrum δ ppm (DMSO-d$_6$): 1.3 (3H, s, α-CH$_3$), 2.9 to 3.3 (2H, m, α-CH$_2$), 5.6 (2H, s, NH$_2$), 5.9 (2H, s, CH$_2$), 7.0 (1H, s, NH) and 6.4 to 6.8 (3H, m, aromatic).

Infrared absorption spectrum (cm$^{-1}$, KBr-disk): 3500, 3400, 3330, 2900, 1695, 1600, 1570, 1490, 1440, 1390, 1280 and 1245.

$[\alpha]_D^{25} = +92.0$ (c=0.5, 0.1N NaOH).

Melting point: 190° to 192° C.

On the other hand, 1000 ml of water was added to the insoluble mixture and the resultant was adjusted to a pH value of 11.5 with a 10N NaOH solution. After stirring for 1 hour to dissolve a crystal existing in the mixture, the cells were removed by further centrifugation. Subsequently, the obtained supernatent was adjusted to a pH value of 7.0 with a 6N HCl solution to form a white crystal, which was filtered and recrystallized from ethanol to give 6.7 g of (R)-4'-methyl-4'-(3,4-methylenedioxyphenylmethyl)-imidazolidine-2',5'-dione as a white crystal.

Nuclear magnetic resonance spectrum δ ppm (DMSO-d$_6$): 1.3 (3H, s, α-CH$_3$), 2.8 (2H, q, α-CH$_2$), 5.9 (2H, s, CH$_2$), 6.5 to 6.8 (3H, m, aromatic), 7.9 (1H, s, NH) and 10.3 (1H, s, NH).

Infrared absorption spectrum (cm$^{-1}$, KBr-disk): 3340, 3190, 3070, 2895, 1760, 1710, 1505, 1490, 1440, 1405, 1300, 1280 and 1245.

$[\alpha]_D^{25} = +63.6$ (c=0.5, 0.1N NaOH)

Melting point: 226° to 229° C.

EXAMPLE 5

A mixture of 5.0 g of (S)-N-carbamoyl-α-methyl-3,4-methylenedioxyphenylalamine, 25 g of crystal of barium hydroxide and 125 ml of water was boiled under reflux. After the reaction was completed, 125 ml of water was further added to the mixture and the resultant was adjusted to a pH value of 1.8 with dilute sulfuric acid. A formed precipitate of barium sulfate was filtered and a filtrate was decolorized with decolorizing carbon at heating and concentrated under reduced pressure. To a residue was added 80 ml of 20 % aqueous solution of hydrochloric acid and 4 g of phenol and a mixture was refluxed under stirring for 19 hours. After the reaction was completed, an oily product was separated and removed from the reaction mixture and an excess of hydrochloric acid was distilled away under reduced pressure. To an obtained residue was added 10 ml of water to dissolve at heating and the resultant solution was decolorized with decolorizing carbon, which was then adjusted to a pH value of 6.0 with 5N aqueous solution of ammonium containing a small amount of sodium bisulfite and was allowed to stand for a night in the refrigerator. A precipitated crystal was filtered and washed with a small amount of cooled water, which was then dried to give 3.2 g of (S)-α-methyl-3,4-dihydroxyphenylalanine 3/2 hydrate.

$[\alpha]_D^{25} = -5.5$ (c=2.0, 1N HCl).

Melting point: 306° to 307° (dec.).

EXAMPLE 6

After preparing a liquid nutrient medium having the following composition, each 500 ml shaking flask stuffed with cotton was filled with 100 ml of the medium and steam-sterilized at 120° C. for 20 minutes.

| [composition] | |
|---|---|
| meat extract | 0.5% (W/V %) |
| yeast extract | 0.5% |
| polypeptone | 1.0% |
| NaCl | 0.3% |
| uracil | 0.1% |
| manganese chloride tetrahydrate | 20 ppm |
| pH | 7.0 |

A loop of *Corynebacterium sepedonicum* (IFO) 13259) which was previously cultivated on bouillon agar slant at 33° C. for 24 hours inoculated into the above medium and subjected to a shake culture at 3320 C. for 24 hours. After centrifuging 200 ml of the culture solution, the obtained cells were washed with 200 ml of 0.9% aqueous solution of salt. After further centrifugation, the cells suspension was prepared by adding 0.9% aqueous solution of salt to the cells so as to become 40 ml as a total amount.

For the reaction, the following solution and suspension were prepared.

(1) A solution of 2.40 g of (RS)-N-carbamoyl-α-methylleucine dissolved as a sodium salt (pH 7.2) and prepared to become 40 ml as a total amount (2) The cells suspension prepared as mentioned above A mxiture of the above solution (1) and the suspension (2) was put into a 200 ml four-necked round flask and was reacted with stirring at 37° C. for 20 hours. During the reaction, a pH value in the reaction system was continuously maintained at 7.2 with a 0.5N HCl solution. After the reaction was completed, the reaction mixture was centrifuged to remove the cells. The obtained supernatent was readjusted to a pH value of 7.0 and extracted twice with 100 ml of ethyl acetate. After distilling away ethyl acetate under reduced pressure, 10.42 g of (R)-4-methyl-4-isobutylimidazolidine-2,5-dione was obtained as a white crystal.

Nuclear magnetic resonance spectrum δ ppm (DMSO-d$_6$): 1.8 (6H, t, CH$_3$), 1.3 (3H, s, α-CH$_3$), 1.4 to 1.8 (3H, m, CH$_2$CH$_2$), 7.9 (1H, s, NH) and 10.6 (1H, s, NH).

Infrared absorption spectrum (cm$^{-1}$, KBr-disk): 3200, 3050, 2950, 1760, 1705, 1570, 1430, 1370, 1280, 1230 and 1200.

$[\alpha]_D^{25} = +0.8$ (c=0.5, 0.1N NaOH).

Melting point: 131° to 134° C.

Water phase treated with ethyl acetate extraction was adjusted to a pH value of 1.0 and again extracted with 100 ml×2 of ethyl acetate. After distilling away ethyl acetate from an extract under reduced pressure, 1.10 g of (S)-N-carbamoyl-α-methylleucine was obtained as a white crystal $[\alpha]_D^{25} = +8.0$ (c=0.5, 0.1N NaOH)). To 25 ml of a 2N aqueous solution of HCl was added 1.00 g of the thus obtained (S)-N-carbamoyl-α-methylleucine and a mixture was heated at 80° C. for 2 hours in order to cyclize to give 0.83 g of (S)-4-methyl-4-isobutylimidazolidine-2,5-dione as a white crystal.

$[\alpha]_D^{25} = -0.8$ (c=0.5, 0.1N NaOH).

Melting point: 131° to 134° C.

EXAMPLE 7

A loop of Nocardia corallina (IFO 3338) which was previously cultivated on bouillon agar slant at 30° C. for 24 hours was inoculated into the above liquid nutrient medium prepared as in Example 6 and subjected to a shake culture at 30° C. for 24 hours. After centrifuging 200 ml of the culture solution, the obtained living cells were washed with 200 ml of 0.9 % aqueous solution of salt. Afer further centrifugation, cells suspension was prepared by adding 0.9% aqueous solution of salt to the cells so as to become 40 ml as a total amount.

For the reaction, the following solution and suspension were prepared.

(1) A solution of 2.40 g of (RS)-N-carbamoyl-α-methyl-leucine dissolved as a sodium salt (pH 7.2) and prepared to become 40 ml as a total amount
(2) The cells suspension prepared as mentioned above A mxiture of the above solution (1) and the suspension (2) was put into a 200 ml four-necked round flask and was reacted with stirring at 37° C. for 20 hours. During the reaction, a pH value in the reaction system was continuously maintained at 7.2 with a 0.5N HCl solution. After the reaction was completed, the reaction mixture was cooled and adjusted to a pH value of 7.0 and an insoluble mixture of a crystal precipitated in the reaction and a supernatent were separated by centrifugation. To the insoluble mixture was added 200 ml of water and the resultant was adjusted to a pH value of 11.5 with 10N NaOH solution. After stirring for 1 hour to dissolve a crystal existing in the mixture, the cells were removed by further centrifugation. Subsequently, the obtained supernatent was adjusted to a pH value of 7.0 with 6N HCl solution to form a white crystal, which was filtered and recrystallized from ethanol to give 1.03 g of (R)-4-methyl-4-phenylimidazolidine-2,5-dione as a white crystal.

Nuclear magnetic resonance spectrum δ ppm (DMSO-d$_6$): 1.7 (3H, s, α-CH$_3$), 7.3 to 7.6 (5H, m, aromatic), 8.6 (1H, s, NH) and 10.8 (1H, s, NH).

Infrared absorption spectrum (cm$^{-1}$, KBr-disk): 3280, 3210, 1765, 1710, 1495, 1440, 1400, 1365, 1250 and 1230.

$[\alpha]_D^{25} = -141$ (c=0.5, 0.1N NaOH).

Melting point: 240° to 242° C.

On the other hand, a white precipitate was formed by adjusting a pH value of the supernatent to 1.0 using a 6N HCl solution. After the precipitate was filtered and washed with water sufficiently, the resultant was dried under reduced pressure to give 1.07 g of (S)-N-carbamoyl-α-methylphenylglycine $[\alpha]_d^{25} = +52$ (c=0.5, 0.1N NaOH)). To 20 ml of 2N H$_2$SO$_4$ solution was added 0.80 g of the thus obtained (S)-N-carbamoyl-α-methylphenylglycine and a suspension was heated with stirring at 80° C. for 3.5 hours for the cyclization reaction. After cooling, a precipitated crystal was filtered and recrystallized from ethanol to give 0.68 g of (S)-4-methylphenylimidazolidine-2,5-dione.

$[\alpha]_D^{25} = +139.5$ (c=0.5, 0.1N NaOH).

Melting point: 240° to 242° C.

EXAMPLE 8

The same procedures as in Example 2 were repeated except that a racemic 4-carbamoylamino-6-fluoro-2-methylchroman-4-carboxylic acid (a mixture of a (2S,4R) form and a (2R,4S) form) was used as a substrate instead of (RS)-4-carbamoylamino-6-fluorochroman-4-carboxylic acid. There was obtained 0.49 g of a white crystal of (2S,4R)-6-fluoro-2-methyl-spiro-[chroman-4,4'-imidazolidine]-2',5'-dione from an ethyl acetate extract.

$[\alpha]_D^{20} = -224$ (c=1.0, EtOH).

Melting point: 250° to 252° C.

On the other hand, a precipitate obtained from a supernatant of the centrifuged reaction mixture was treated with the same procedures as in Example 3, thereby (2R,4S)-N-carbamoylamino-6-fluoro-2-methyl-chroman-4-carboxylic acid is cyclized by heating to give 0.45 g of (2R,4S)-6-fluoro-2-methyl-spiro-[chroman-4,4'-imidazolidine]-2',5'-dione as a white crystal.

$[\alpha]_D^{25} = +225$ (c=1.0, EtOH).

Melting point: 250° to 252° C.

What we claim is:

1. A process for preparing an optically active hydantoin having the general formula (II):

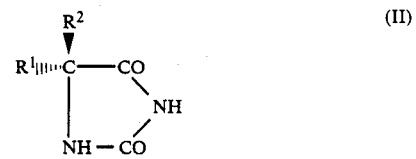

(II)

wherein R$^1$ and R$^2$, which are different from each other, are independently alkyl group, aralkyl group, aryl group, substituted alkyl group, substituted aralkyl group, or substituted aryl group, or R$^1$ and R$^2$ form an asymmetric cyclic compound, which comprises subjecting a racemic N-carbamoyl-α-amino acid having the general formula (I):

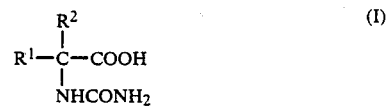

(I)

wherein R$^1$ and R$^2$ are as above, to the action of an enzyme capable of converting one enantiomer of said N-carbamoyl-α-amino acid to said optically active hydantoin, and recovering said optically active hydantoin.

2. The process of claim 1, where in thr N-carbamoyl-α-amino acid having the general formula (I) is a 4-carbamoylaminochroman-4-carboxylic acid having the general formula (I):

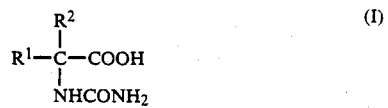

(I)

wherein R$^1$ and R$^2$ is the formula:

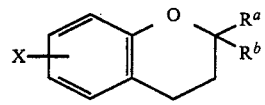

wherein X is a halogen atom, and R$^a$ and R$^b$ is hydrogen atom or methyl group.

3. The process of claim 1, wherein one of R$^1$ and R$^2$ is a member selected from the group consisting of 3,4-methylenedioxphenylmethyl group and 3,4-dimethoxyphenylmethyl group and the other is methyl group.

4. The process of claim 1, wherein the hydantoin has the (R)-configuration.

5. The process of claim 2, wherein the hydantoin is (4R)-6-fluoro-2-spiro-[chroman-4,4'-imidazolidine]-2',5'-dione having the formula:

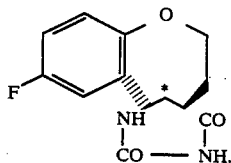

6. The process of claim, 2, wherein the hydantoin is (4R)-6-fluoro-2-methyl-spiro-[chroman-4,4'-imidazolidine]-2',5'-dione having the formula:

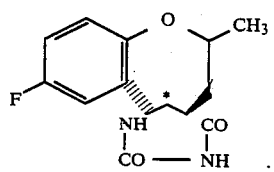

7. The process of claim 1, wherein the enzyme is a cultured broth of a microorganism, cells of a microorganism or treated cells of a microorganism.

8. The process of claim 7, wherein the microorgsnism is selected from the genera consisting of Aerobsacter, Agrobacterium, Bacillus, Corynebsacterium and Nocardia.

9. The process of claim 1, wherein the enzyme is at a ph of from 5 to 8.

10. The process of claim 1, wherein the unreacted enantiomer of N-carbamoyl-α-amino acid is separated from the hydantoin and recovered as an optically active N-carbamoyl-α-amino acid having the general formula (III):

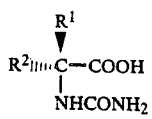

wherein $R^1$ and $R^2$ are as above.

11. A process for preparing an optically active amino acid having the general formula (VI):

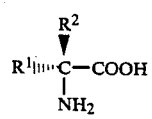

wherein $R^1$ and $R^2$, which are different from each other, are independently alkyl group, aralkyl group, aryl group, substituted alkyl group, substituted aralkyl group, or substituted aryl group, or $R^1$ and $R^2$ form an asymmetric cyclic compound, which comprises subjecting a racemic N-carbamoyl-α-amino acid having the general formula (I):

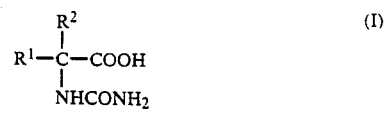

wherein $R^1$ and $R^2$ are as above, to the action of an enzyme capable of converting one enantiomer of said amino acid to the corresponding hydantoin, separating the thus formed hydantoin from the unreacted N-carbsamoyl-α-amino acid, and hydrolyzing the hydantoin with alkali.

12. A process for preparing an optically active hydantoin having the general formula (IV):

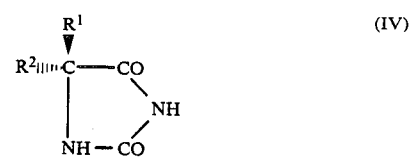

wherein $R_1$ and $R_2$, which are different from each other, are independen tly alkyl group, aralkyl group, aryl group, substituted alkyl griup, substituted aralkyl group, or substituted aryl group, or $R_1$ and $R_2$ form an asymmetric cyclic compound, which omprises subjecting a racemic N-carbamoyl-α-amino acid having the general formula (I):

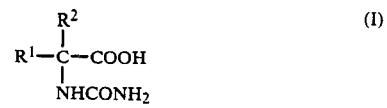

wherein $R^1$ and $R^2$ are as above, to the action of an enzyme capable of converting one enantiomer of said amino acid to the corresponding hydantoin, separating the unreacted optically active N-carbamoyl-α-amino acid from the thus formed hydantoin, and cyclizing the unreacted optically active N-carbamoyl-α-amino acid under acidic conditions to form optically active hydantoin (IV):

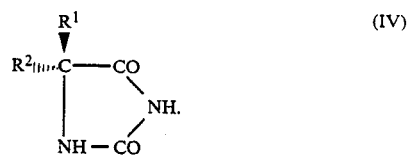

13. The process of claim 12, wherein the N-carbamoyl-α-amino acid having the general formula (1) is 4-carbamoylaminochroman-4-carboxylic acid having the general formula (I):

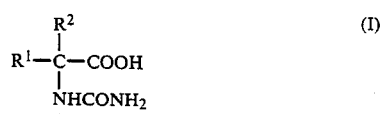

wherein $R^1$ and $R^2$ is the formula:

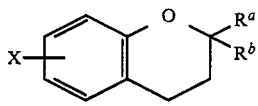

wherein X is a halogen atom, and $R^a$ and $R^b$ is hydrogen atom or methyl group.

14. The process of claim 12, wherein the optically active N-carbamoyl-α-amino acid has the (S) configuration.

15. A process for preparing an optically active amino acid which comprises subjecting a racemic N-carbamoyl-α-amino acid having the general formula (I):

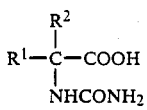

wherein $R^1$ and $R^2$, which are different from each other, are independently alkyl group, aralkyl group, aryl group, substituted alkyl group, substituted aralkyl group, or substituted aryl group, or $R^1$ and $R^2$ form an asymmetric cyclic compound, to the action of an enzyme capable of converting one enantiomer of said amino acid to the corresponding hydantoin, separating the optically active N-carbamoyl-α-amino acid from the thus formed hydantoin, and hydrolyzing the unreacted optically active N-carbamoyl-α-amino acid with alkali to form the corresponding optically active amino acid.

16. The process of claim 15, wherein one of $R^1$ and $R^2$ is a member selected from the group consisting of 3,4-methylenedioxphenylmethyl or 3,4-dimethoxyphenylmethyl group and the other is methyl group.

* * * * *

UNITED STATES PATENT AND TRADEMARK OFFICE
CERTIFICATE OF CORRECTION

PATENT NO. : 4,812,406
DATED : March 14, 1989
INVENTOR(S) : TAKAHASHI et al

It is certified that error appears in the above-indentified patent and that said Letters Patent is hereby corrected as shown below:

On the cover page, Item [57], formula (II) should read:

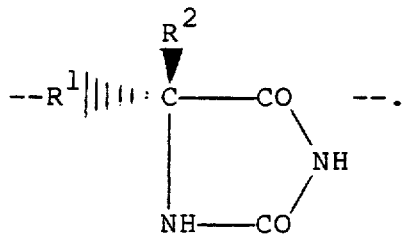

Column 1, line 14, "hydantoins of" should read --Hydantoins cf--.

Column 2, in the scheme after line 41, "Δ+H-" should read --Δ+H+--.

Column 3, line 16, "cyaho" should read --cyano--;
        line 54, "to,the" should read --to the--.

Column 4, line 65, "5." should read --5,--.

Column 5, line 4, "heutralizing" should read --neutralizing--;
        line 9, "temeprature" should read --temperature--;
        line 20, "Generaly," should read --Generally,--;
        line 34, "insolubile" should read --insoluble--;
        line 45, "70 to 100° C" should read --70° to 100° C--.

Column 6, line 8, "αamino" should read --α-amino--;
        line 28, "polypentone" should read --polypepton--.

Column 7, line 11, "imidazolidine-2',5'-" second occurrence
    should read -- imidazolidine]-2',5'- --;
        line 49, "Bacillus species" should read
    --<u>Bacillus species</u>--.

UNITED STATES PATENT AND TRADEMARK OFFICE
CERTIFICATE OF CORRECTION

PATENT NO. : 4,812,406
DATED : March 14, 1989
INVENTOR(S) : TAKAHASHI et al

Page 2 of 5

It is certified that error appears in the above-indentified patent and that said Letters Patent is hereby corrected as shown below:

Column 8, line 42, "Melting point. 196° to 197° C." should be deleted;
    line 61, "Bacillus species" should read --*Bacillus species*--.

Column 9, line 1, "reation" should read --reaction--;
    line 2, "reation" should read --reaction--;
    line 4, "supernatent" should read --supernatant--;
    line 6, "supernatent" should read --supernatant--;
    line 26, "supernatent" should read --supernatant--;
    line 44, "methylenedioxyphenylalamine" should read --methylenedioxyphenylalanine--.

Column 10, line 21, "3320 C." should read --33° C.--;
    line 42, "supernatent" should read --supernatant--;
    line 61, "[α]" should read --([α]--.

Column 11, line 3, "Nocardia corallina" should read --*Nocardia corallina*--;
    line 27, "supernatent" should read --supernatant--;
    line 33, "supernatent" should read --supernatant--;
    line 47, "supernatent" should read --supernatant--;
    line 51, "[α]" should read --([α]--.

UNITED STATES PATENT AND TRADEMARK OFFICE
CERTIFICATE OF CORRECTION

PATENT NO. : 4,812,406

DATED : March 14, 1989

INVENTOR(S) : TAKAHASHI et al

Page 3 of 5

It is certified that error appears in the above-indentified patent and that said Letters Patent is hereby corrected as shown below:

Column 12, line 7, "supernatent" should read --supernatant--;
line 45, "where in thr" should read --wherein the--;
line 60, the formula should read:

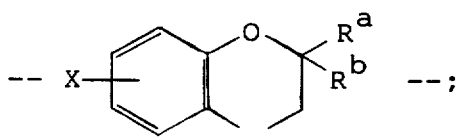

line 67, "methylenedioxphenylmethyl" should read --methylenedioxyphenylmethyl--.

Column 13, line 4, "fluoro-2-spiro" should read --fluoro-spiro--;

Column 13, lines 6 to 14, the formula should read:

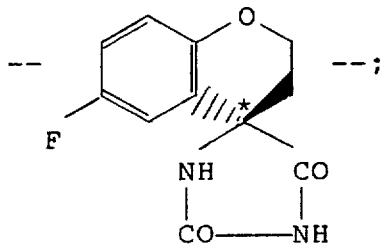

lines 20 to 26, the formula should read:

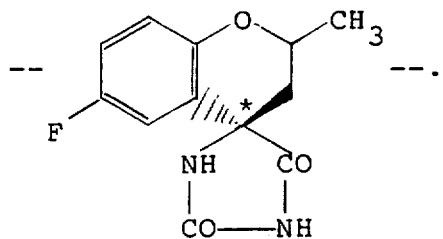

UNITED STATES PATENT AND TRADEMARK OFFICE
CERTIFICATE OF CORRECTION

PATENT NO. : 4,812,406
DATED : March 14, 1989
INVENTOR(S) : TAKAHASHI et al

It is certified that error appears in the above-indentified patent and that said Letters Patent is hereby corrected as shown below:

Column 14, line 12, "samoyl-α-amino" should read
--amoyl-α-amino--;
    line 25, "$R_1$ and $R_2$" should read --$R^1$ and $R^2$--;
    line 26, "independen tly" should read
--independently--;
    line 27, "griup," should read --group,--;
    line 28, "$R_1$ and $R_2$" should read --$R^1$ and $R^2$--;
    line 29, "omprises" should read --comprises--;
    line 46, "conditions" should read --condition--;
    line 58, "(l)" should read --(I)--.

Column 15, lines 1 to 9, the formula should read:

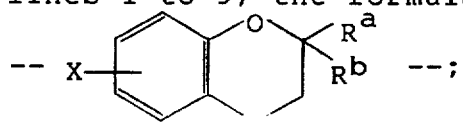

Column 15, line 21, after "acid" the following should be inserted:

--having the formula (V):

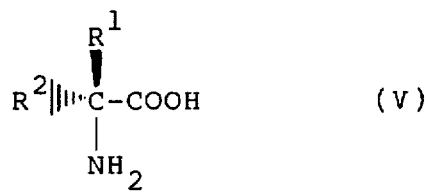

UNITED STATES PATENT AND TRADEMARK OFFICE
CERTIFICATE OF CORRECTION

PATENT NO. : 4,812,406
DATED : March 14, 1989
INVENTOR(S) : TAKAHASHI et al

It is certified that error appears in the above-indentified patent and that said Letters Patent is hereby corrected as shown below:

wherein $R^1$ and $R^2$, which are different from each other, are independently alkyl group, aralkyl group, aryl group, substituted alkyl group, substituted aralkyl group, or substituted aryl group, or $R^1$ and $R^2$ form an asymmetric cyclic compound,--.

Column 16, lines 7 to 11, "which are different from each other, are independently alkyl group, aralkyl group, aryl group, substituted alkyl group, substituted aralkyl group, or substituted aryl group, or $R^1$ and $R^2$ form an asymmetric cyclic compound" should read --are as above--;
    line 14, "the optically" should read --the unreacted optically--;
    line 21, "methylenedioxphenylmethyl" should read --methylenedioxyphenylmethyl--.

Signed and Sealed this

Twenty-seventh Day of December, 1994

Attest:

BRUCE LEHMAN

Attesting Officer     Commissioner of Patents and Trademarks